United States Patent [19]

Hesse

[11] Patent Number: Plant 6,936

[45] Date of Patent: Jul. 18, 1989

[54] CHRYSANTHEMUM PLANT NAMED NEON

[75] Inventor: Peter S. Hesse, Bradenton, Fla.

[73] Assignee: Ball Seed Company, West Chicago, Ill.

[21] Appl. No.: 139,766

[22] Filed: Dec. 30, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Neon having vibrant hot pink ray florets and yellow disc florets which fade to a light pink as the flower matures, anemone flower type, 7 week flowering response, and a tendency for the ray florets to fade to white at the apex and margins as the flowers fade.

1 Drawing Sheet

The present invention comprises a new and distinct cultivar of *Chrysanthemum morifolium,* hereinafter referred to by the cultivar name Neon.

Neon is a product of a planned breeding program which had the objective of creating new Chrysanthemum cultivars with compact habit, early flower response, anemone type flower, and dark purple ray floret color, all of which characteristics make Neon ideally suited for production as a garden mum. Such traits in combination were not present or needed improvement in previously available commercial cultivars.

Neon was originated from a hybridization made by appicant in a controlled breeding program in Parrish, Fla., in 1984. The female parent was Viva. The male parent of Neon was Volunteer. Neon was discovered and selected as one flowering plant within the progeny of the stated parentage by applicant in November 1984 in a controlled environment in Parrish, Fla.

The first act of asexual reproduction of Neon was accomplished when vegetative cuttings were taken from the initial selection in March 1985 in a controlled environment in Parrish, Fla. by a technician working under formulations established and supervised by applicant. Horticultural examination of selected units initiated in September 1985 has demonstrated that the combination of characteristics as herein disclosed for Neon are firmly fixed and are retained through successive generations of asexual reproduction.

The following traits have been repeatedly observed and are determined to be basic characteristics of Neon, which in combination distinguish this Chrysanthemum as a new and distinct cultivar:

1. Seven week flowering response.
2. Vibrant hot pink ray florets and golden yellow immature disc florets. When the disc florets open or expand as the flower matures, a red purple base is clearly visible through the golden yellow disc florets.
3. The disc florets fade to a light pink as the flower continues to mature.
4. Anemone flower type.
5. Under high (85° F.+) temperatures Neon occasionally appears bi-colored; ray florets are dark pink near the disk and fade to white at the apex and margins.
6. Ray florets are up to approximately 29 mm long and 8 mm wide.
7. Entire flower diameter is 5 to 6 cm.
8. At full maturity the disc florets reach up to 13 mm in length, and are zygomorphic and funnelform.

9. Suitable for use as a garden mum for production in 4½" to 1 gallon containers.

Neon has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Neon is Carmella. In comparison to Carmella, Neon has a one week faster flowering response, dark pink flower color and a more compact growth habit. The flower form and type are similar to the same characteristics of Carmella.

The accompanying photographic drawings show typical inflorescence and foliage characteristics of Neon. The first sheet comprises a black and white photograph with a single flower being colored to show the true ray and disc floret color of Neon. The second sheet is also in black and white, showing in color a single flower grown under high temperatures. The white margins and apex of each ray floret will be apparent.

In the following description, color references are made to The Royal Horticultural Society Colour Chart. The color values were determined between 10:00 and 10:30 a.m. on Oct. 21, 1987 under fluorescent light at Parrish, Fla.

Classification:

*Botanical.*—*Chrysanthemum morifolium,* cv. Neon.
*Commercial.*—Anemone garden mum.

INFLORESCENCE

A. Capitulum:
*Form.*—Flat.
*Type.*—Anemone.
*Diameter across face.*—5 to 6 cm.

B. Corolla of ray florets:
*Color (general tonality from a distance of three meters).*—Dark hot pink.
*Color (back).*—74C.
*Color (top).*—72B.

It should be noted these color values were not taken under the high temperatures noted above at or above which the ray florets tend to fade at the margins and apex.

C. Corolla of disc florets:

*Color* (*immature*).—Golden yellow when discs are tight at opening; as flower matures and discs expand, a purple base is visible through golden yellow tips.

*Color* (*mature*).—69B.

D. Reproductive organs:

*Androecium.*—Present in disc florets only.

*Gynoecium.*—Present in both disc and ray florets.

PLANT

A. General appearance:

*Height.*—21 cm when grown in the ground, given no long days and one pinch. Height will vary depending upon growing conditions.

B. Foliage:

*Color* (*upper surface*).—147A.

*Color* (*under surface*).—147B.

*Shape.*—Ovate, deeply lobed and slightly serrate margins.

I claim:

1. A new and distinct cultivar of Chrysanthemum plant named Neon, as illustrated and described.

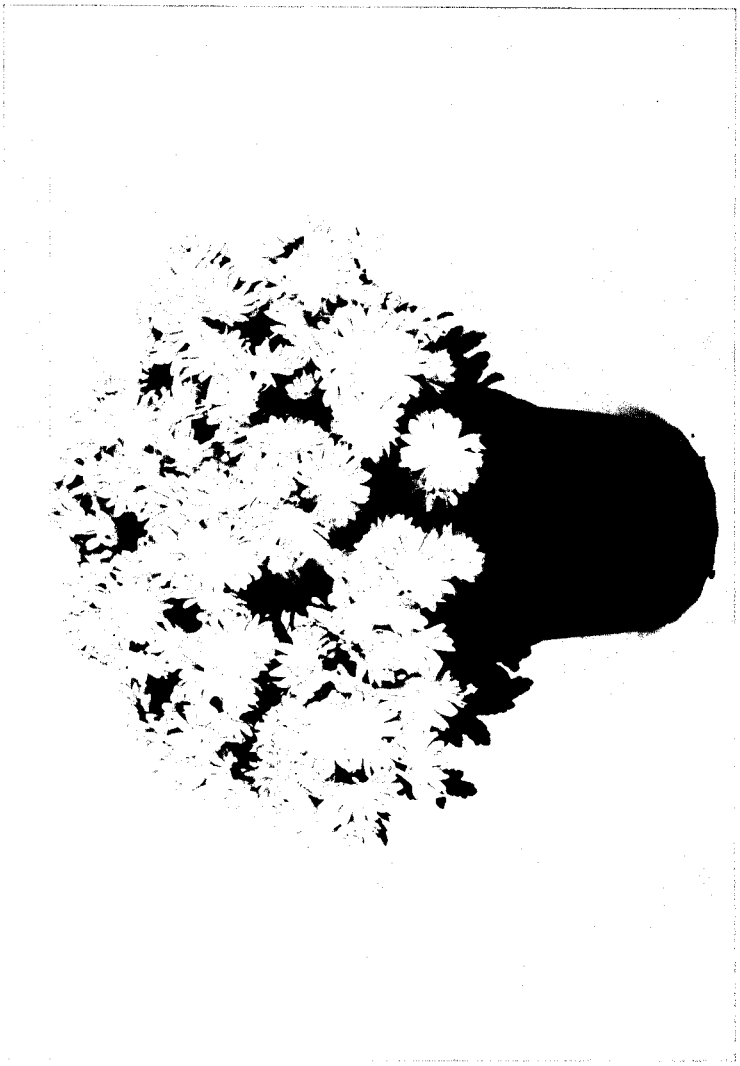

* * * * *